US008861685B2

(12) United States Patent
Pohan

(10) Patent No.: US 8,861,685 B2
(45) Date of Patent: Oct. 14, 2014

(54) SCATTERED-RADIATION COLLIMATOR AND METHOD FOR PRODUCING A SCATTERED RADIATION COLLIMATOR

(75) Inventor: Claus Pohan, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 915 days.

(21) Appl. No.: 12/941,398

(22) Filed: Nov. 8, 2010

(65) Prior Publication Data
US 2011/0108745 A1    May 12, 2011

(30) Foreign Application Priority Data
Nov. 10, 2009 (DE) .................. 10 2009 052 627

(51) Int. Cl.
G21K 1/00 (2006.01)
G21K 1/10 (2006.01)
G21K 1/02 (2006.01)
A61B 6/03 (2006.01)
A61B 6/00 (2006.01)

(52) U.S. Cl.
CPC ............... *G21K 1/025* (2013.01); *A61B 6/032* (2013.01); *A61B 6/4291* (2013.01)
USPC ......................................................... 378/154

(58) Field of Classification Search
CPC ............................... G21K 1/02; G21K 1/025
USPC ..................... 378/19, 98.8, 147, 149, 154; 250/370.09
See application file for complete search history.

(56) References Cited

U.S. PATENT DOCUMENTS 6,055,296 A   4/2000 Ferlic et al.
6,363,136 B1  3/2002 Flisikowski et al.
(Continued)

FOREIGN PATENT DOCUMENTS

DE  19852048 A1  5/2000
DE  19947537 A1  4/2001
DE  10009285 A1  8/2001
DE  10011877     8/2002

OTHER PUBLICATIONS

Office Action for corresponding Chinese patent application No. 201010546027.2 dated Jan. 22, 2014.

*Primary Examiner* — Allen C. Ho
(74) *Attorney, Agent, or Firm* — Harness, Dickey & Pierce, P.L.C.

(57) ABSTRACT

A scattered-radiation collimator is disclosed for radiological radiation with a multiplicity of absorber elements that are arranged one behind the other in a collimation direction and held in a support frame. In at least one embodiment, the support frame includes a holding device for holding the absorber elements on opposite sides across the collimation direction, and at least one strip-like holding element spans the absorber elements in a collimation direction on the radiation entry side and/or the radiation exit side of the scattered-radiation collimator and additionally fixes the absorber elements on the longitudinal edges thereof in a mechanical fashion. In at least one embodiment, the holding elements prevent deformations of long absorber elements caused by centrifugal forces to a large extent. This affords the possibility of implementing scattered-radiation collimators with a large Z-coverage that meet the demand on the absorber elements in respect of dimensional stability and positional accuracy. Moreover, at least one embodiment of the invention relates to a method for producing such a scattered-radiation collimator.

16 Claims, 4 Drawing Sheets

(56) References Cited

U.S. PATENT DOCUMENTS

| | | | |
|---|---|---|---|
| 6,396,898 B1 * | 5/2002 | Saito et al. | 378/19 |
| 6,470,067 B1 | 10/2002 | Harding | |
| 6,587,538 B2 * | 7/2003 | Igarashi et al. | 378/19 |
| 6,687,334 B2 | 2/2004 | Galish et al. | |
| 7,235,790 B2 * | 6/2007 | Hoge | 250/370.11 |
| 7,236,560 B2 * | 6/2007 | Malamud | 378/7 |
| 7,257,195 B2 * | 8/2007 | Freund et al. | 378/149 |
| 7,278,192 B2 * | 10/2007 | Schaefer | 29/27 C |
| 7,492,857 B2 * | 2/2009 | Yasunaga et al. | 378/19 |
| 7,526,070 B2 * | 4/2009 | Igarashi et al. | 378/149 |
| 7,560,702 B2 * | 7/2009 | Meirav et al. | 250/370.13 |
| 7,564,940 B2 * | 7/2009 | Mattson et al. | 378/19 |
| 7,573,976 B2 * | 8/2009 | Lacey | 378/19 |
| 7,630,476 B2 * | 12/2009 | Sakuta | 378/149 |
| 8,126,119 B2 * | 2/2012 | Kurochi | 378/147 |
| 2005/0135562 A1 | 6/2005 | Freund et al. | |

* cited by examiner

SCATTERED-RADIATION COLLIMATOR AND METHOD FOR PRODUCING A SCATTERED RADIATION COLLIMATOR

PRIORITY STATEMENT

The present application hereby claims priority under 35 U.S.C. §119 on German patent application number DE 10 2009 052 627.7 filed Nov. 10, 2009, the entire contents of which are hereby incorporated herein by reference.

FIELD

At least one embodiment of the invention generally relates to a scattered-radiation collimator for radiological radiation and/or a method for producing such a scattered-radiation collimator.

BACKGROUND

It is well known that scattered radiation impairs image quality, particularly in the case of imaging tomography scanners, such as e.g. in the case of computed tomography scanners. In order to reduce the detected proportion of the scattered radiation in the detector signals, so-called scattered-radiation collimators are arranged upstream of the radiation detectors in such computed tomography scanners.

By way of example, known scattered-radiation collimators comprise absorber elements, which are arranged next to one another in a collimation direction and are aligned unidirectionally in respect of their longitudinal extent. The absorber surfaces of the absorber elements are aligned radially in a fan-like shape with respect to the focus of a radiation source, and so only radiation from a spatial direction directed at the focus can impinge on the radiation detector. The radiation from this spatial direction is usually also referred to as primary radiation. Scattered radiation is substantially generated as a result of interaction processes between the primary radiation and the object to be examined. Scattered-radiation components that impinge on the scattered-radiation collimator from a different spatial direction than the primary radiation are mostly absorbed by the absorber surfaces. This affords a reduction in image artifacts caused by scattered-radiation effects in the reconstructed image.

The absorber elements of the scattered-radiation collimators are generally comparatively thin and delicate. As a result of this, they have, as such, low mechanical stability and are therefore not very dimensionally stable. Particularly when the recording system in a computed tomography scanner rotates, centrifugal forces and transverse forces perpendicular to the collimation direction are exerted on the absorber elements, causing deformations in the absorber elements and hence can lead to artifacts in the recorded attenuation values and hence in the reconstructed image, for example as a result of shadowing the detector elements.

In order to avoid deformations and temporary displacements, or in order to increase the stability of the absorber elements, two different approaches are substantially followed when a scattered-radiation collimator is implemented. The absorber elements of the scattered-radiation collimator are held in a support frame in the form of a plastics housing in a first approach. The plastics housing has very precise corresponding cut-outs on opposite sides of the support frame for a hold across the collimation direction. In this case, the scattered-radiation collimator is dimensioned such that it integrally spans the radiation detector in the z-direction. Such a scattered-radiation collimator is also referred to as a bridge collimator. However, a disadvantage of this embodiment is that, in particular, only very limited lengths of such a scattered-radiation collimator can be produced for injection-molding technical reasons, and so these scattered-radiation collimators can only be used in radiation detectors of a limited length or a restricting Z-coverage. However, radiation detectors are increasingly being designed with an ever increasing number of detector rows and hence with an increased coverage in the z-direction. Using bridge collimators in such radiation detectors is becoming evermore difficult for this reason.

In another approach, the scattered-radiation collimators are produced in small units and bonded onto the radiation detector in a tiled shape or like a matrix. Hence, scattered-radiation collimators with a comparatively large Z-coverage can be assembled, that is to say they can also be assembled for radiation detectors with a multiplicity of detector rows. Such a scattered-radiation collimator is also referred to as a tile collimator. However, a disadvantage of these scattered-radiation collimators is that, in particular, there is the risk of gaps forming at the seams that have to be present between adjacent scattered-radiation collimators as a result of the tile-shape design, through which gaps scattered radiation can impinge on the detector elements.

Moreover, in future there will also be higher mechanical demands on scattered-radiation collimators. Previously, rotational speeds of 210 rpm have been reached by the recording system in computed tomography scanners during examination operation. However, in future, the rotational speeds should be increased to at least 300 rpm. As a result of the higher centrifugal and transverse forces thereby exerted on the scattered-radiation collimator, the demands on dimensional stability are becoming evermore important.

SUMMARY

In at least one embodiment of the invention, a scattered-radiation collimator is disclosed in which absorber elements arranged in the scattered-radiation collimator have a high dimensional stability, even at high rotational speeds and in the case of large z-coverage. Moreover, a method is disclosed for producing such a scattered-radiation collimator should be specified.

In at least one embodiment is directed to a scattered-radiation collimator, and at least one embodiment is directed to a method for producing a scattered-radiation collimator. Advantageous refinements and developments are the subject matter of dependent claims.

The scattered-radiation collimator according to at least one embodiment of the invention for radiological radiation comprises a multiplicity of absorber elements that are arranged one behind the other in a collimation direction and held in a support frame, wherein the support frame has a holding device for holding the absorber elements on opposite sides across the collimation direction. According to at least one embodiment of the invention, at least one strip-like holding element is provided on the radiation entry side and/or the radiation exit side of the scattered-radiation collimator, which at least one strip-like holding element spans the absorber elements in a collimation direction and additionally fixes said absorber elements on the longitudinal edges thereof in a mechanical fashion.

The additional mechanical fixing of the longitudinal edges of the absorber elements to the strip-like holding element ensures that the absorber elements remain stabile in terms of position and alignment, even in the case of a large Z-coverage and at high rotational speeds. This is because the attached strip-like holding element compensates the respectively oppositely directed transverse forces that occur in the outer regions of the absorber elements, particularly during rotation of the recording system. In the process, the holding element is only loaded with tensile stress and thus prevents the absorber elements from sagging.

Thus, the inventive concept of at least one embodiment allows the absorber elements to be stiffened relative to one another in a simple but nevertheless effective fashion, and so relative displacement, deformation or erroneous positioning of the absorber elements caused by mechanical influences such as e.g. by force influences as a result of rotation or the like, are avoided to the largest possible extent. As a result, a fixed intended position for the absorber elements can be substantially maintained even if forces act, and so artifacts caused by deformations and the like of the absorber elements can be avoided. Thus, a torsionally stiff scattered-radiation collimator, which in particular will meet the demands of future computed tomography scanners, is implemented by using a holding element with a strip-like design.

Here, the term radiation entry side should be understood to be that side of the scattered-radiation collimator that is passed through first by the applied radiation when the scattered-radiation collimator is used as intended. Accordingly, the term radiation exit side should be understood to be that side of the scattered-radiation collimator at which the radiation emerges from the scattered-radiation collimator and subsequently impinges on the radiation detector.

In an advantageous refinement of at least one embodiment of the invention, there are protrusions, more particularly lug-like projections, on the longitudinal edges of the absorber elements, at least on the radiation entry side and/or radiation exit side of the scattered-radiation collimator, for precisely aligning the absorber elements by way of a positioning tool.

Such projections or else protrusions along the longitudinal edge can easily be produced at the same positions along the longitudinal edge for all absorber elements and represent a simple means for being able to hold the absorber elements at a defined position to one another in a positioning tool.

In the collimation direction, the holding element is preferably mounted in each case in the interspace formed by two adjacent protrusions of each absorber element. This allows simple positioning of the holding element on the absorber elements. In the context of positioning the holding element, the protrusions can in this case additionally assume the function of a mechanical stop, for example, by applying the holding element laterally to the respective protrusion during assembly.

In an example embodiment, the longitudinal edges are fixed to the holding element by an adhesive. As a result of using an adhesive there is no need to insert very precise holding device, for example slits, into the holding element. This significantly reduces the overall complexity in the production of such a scattered-radiation collimator. The absorber elements are aligned very precisely during the production process using a positioning tool, which merely needs to be produced once in order to produce a multiplicity of scattered-radiation collimators and which is removed again after the longitudinal edges have been bonded to the holding element. Moreover, an adhesive connection can be produced with little complexity in comparison with other connection methods, for example in comparison with welding or producing screw connections. Thus, for example, a layer of the adhesive can be applied to the holding element on merely one side prior to insertion.

The adhesive advantageously has a low shrinkage property, as is the case in epoxy resins with mineral compounds contained therein. As a result of the low shrinkage property, the absorber elements remain in position even when the adhesive cures.

The strip-like holding element and the support frame are preferably produced from a material with low thermal expansion and/or high X-ray stability, more particularly from fabric-based laminate, CFC or ceramics.

Particularly simple production of the scattered-radiation collimator can be brought about if the support frame is formed from two segment-shaped support elements, which extend in the collimation direction and are arranged opposite to one another and at a distance from one another as a result of two spacer elements arranged across the collimation direction.

According to a second aspect of at least one embodiment of the invention, the production of a scattered-radiation collimator for radiological radiation with a multiplicity of absorber elements arranged one behind the other in a collimation direction is directed to a method, the method comprising a) the absorber elements are positioned in a positioning tool, and in which b) at least one strip-like holding element, provided with an adhesive and spanning the absorber elements, for fixing the absorber elements on the longitudinal edges is positioned on the radiation entry side and/or the radiation exit side of the scattered-radiation collimator.

In an advantageous refinement of at least one embodiment of the invention, the absorber elements are produced with protrusions arranged at respectively the same positions along the one longitudinal edge in step a), wherein the protrusions in the absorber elements matching in terms of the position are inserted into corresponding slits of a positioning element, which extends across the longitudinal direction of the absorber elements, in the positioning tool.

In a further refinement of at least one embodiment of the invention, the holding element is in step b) positioned in an interspace, which is between two of the protrusions and formed in each of the absorber elements.

The absorber elements are preferably fixed on transverse edges or the narrow edges by the support frame between steps a) and b) or after step b). The fixing is preferably brought about by inserting the transverse edges into corresponding holding device, for example slits, of the support frame.

The positioning of the absorber elements in step a) and the fixing of the absorber elements by way of a holding element in step b) are advantageously carried out in a corresponding fashion for the opposing longitudinal edges of the absorber elements as well. Thus, holding elements are arranged on both the radiation entry side and the radiation exit side. This further increases the dimensional stability of the scattered-radiation collimator.

BRIEF DESCRIPTION OF THE DRAWINGS

In the following text, the invention will be explained in more detail on the basis of example embodiments and on the basis of drawings, in which.

DETAILED DESCRIPTION OF THE EXAMPLE EMBODIMENTS

Figure 1:
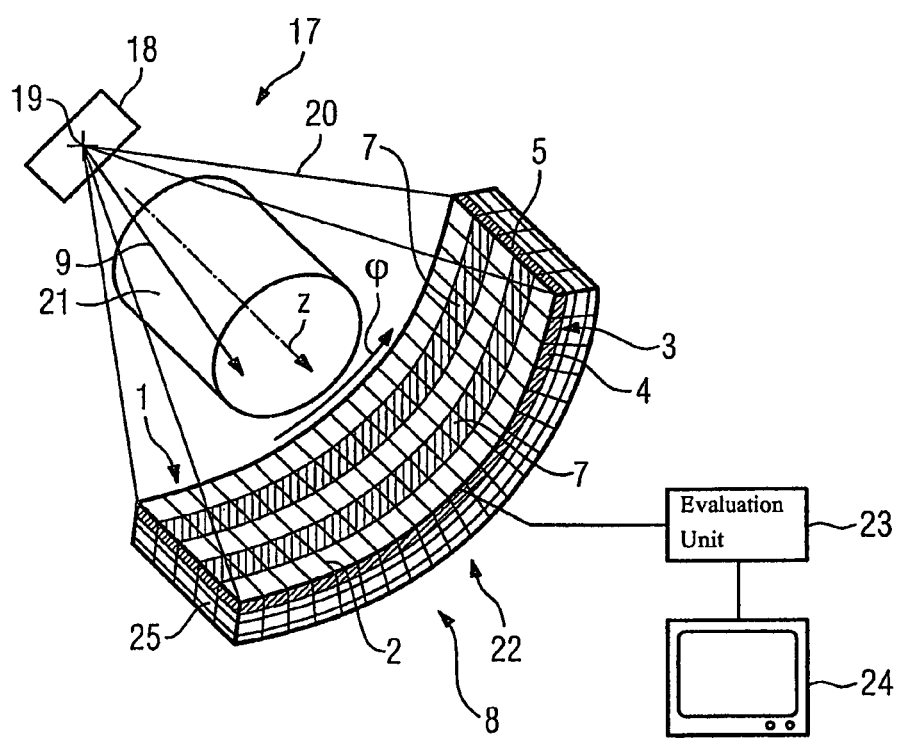
FIG. 1 shows a schematic illustration of a computed tomography scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, parts having the same effect are denoted by the same reference sign. In the case of elements which appear repeatedly in a figure, e.g. the absorber elements 2, only one element has been provided with a reference sign in each case for reasons of clarity. The illustrations in the figures are schematic and not necessarily to scale, wherein scales may vary between the figures.

FIG. 1 shows a computed tomography scanner 17, which comprises a radiation source 18 in the form of an X-ray tube, with an X-ray fan-beam 20 emanating from the focus 19 thereof. The X-ray fan-beam 20 penetrates an object 21 to be examined or a patient and impinges on a radiation detector 22, in this case an X-ray detector.

The X-ray tube 18 and the X-ray detector 22 are arranged opposite to one another on a gantry (not illustrated here) of the computed tomography scanner 17, which gantry can be rotated in a φ-direction around a system axis Z (=patient axis) of the computed tomography scanner 17. The φ-direction thus represents the circumferential direction around the gantry and the Z-direction represents the longitudinal direction of the object 21 to be examined.

During the operation of the computed tomography scanner 17, the X-ray tube 18 and the X-ray detector 22 arranged on the gantry rotate around the object 21, with X-ray recordings of the object 21 being obtained from different projection directions. In each X-ray projection, X-ray radiation that has penetrated the object 21 and has been attenuated thereby impinges on the X-ray detector 22. In the process, the X-ray detector 22 generates signals that correspond to the intensity of the incident X-ray radiation. Subsequently, an evaluation unit 23 calculates one or more two-dimensional or three-dimensional images of the object 21 in a method known per se from the signals registered by the X-ray detector 22 and these images can be displayed on a display unit 24.

The primary radiation emanating from the focus 19 of the X-ray tube 18 is scattered, inter alia, in the object 21, in different spatial directions. This so-called secondary radiation generates signals in the detector elements 25 that cannot be distinguished from the primary radiation signals required for the image reconstruction. Thus, without further measures, the secondary radiation would lead to misinterpretation of the detected radiation and thus to a significant decrease in quality of the images obtained by means of the computed tomography scanner 17.

In order to restrict the influence of the secondary radiation, substantially only the component of the X-ray radiation emanating from the focus 19, that is to say the primary radiation component, is allowed to pass onto the X-ray detector 22 without hindrance by a scattered-radiation collimator 1, whereas the secondary radiation is, in the ideal case, completely absorbed by the absorber surfaces of the absorber elements 2.

In this example embodiment, the scattered-radiation collimator 1 has an integral design and covers the entire X-ray detector 22 in both the φ-direction and the z-direction. However, in the case of a corresponding arrangement of the radiation detector modules, it can also have a plurality of, e.g. four, segments arranged one behind the other in the φ-direction.

The scattered-radiation collimator 1 is assembled from a multiplicity of absorber elements 2. In accordance with the present confocal beam geometry, the absorber elements 2 are aligned in a confocal fashion with a focus 19 of the X-ray tube 18, and are arranged one behind the other in the azimuthal direction φ, which in the present example corresponds to the collimation direction. The absorber elements 2 generally are delicate, fine platelets or sheets with a comparatively small thickness that have an extent in the longitudinal direction substantially corresponding to the Z-coverage of the X-ray detector 22. They are usually made of a radiation-absorbing material, for example tungsten or tantalum, or an alloy with tungsten and/or tantalum as constituents. In the present case, the radiation entry direction 9 corresponds to the radial direction in respect of the focus 19.

Reference is made to the fact that the following refinements consider a scattered-radiation collimator 1 that is used for suppressing scattered radiation in the φ-direction only. However, in this case it is immaterial to an embodiment of the invention whether the scattered-radiation collimator 1 furthermore has additional absorber elements 2 (not illustrated here) for suppressing scattered radiation in the z-direction, which absorber elements are arranged one behind the other in the direction of the z-axis.

Figure 2:
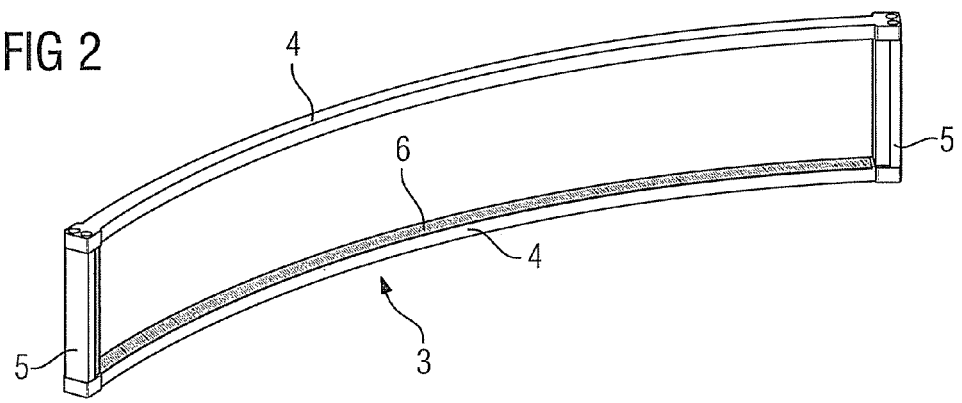
FIG. 2 shows a support frame for the scattered-radiation collimator according to an embodiment of the invention.

FIG. 2 shows a support frame 3 for a scattered-radiation collimator 1 for holding the individual absorber elements 2. For this purpose, the support frame 3 consists of two segment-shaped support elements 4 that are connected to two lateral spacer elements 5. Very precise holding device 6 in the form of slits have been introduced into these support elements 4 in a fan-shaped fashion, with the holding device being used to hold and align the focus of the absorber elements 2 at the shorter sides thereof or on their transverse edges, which are provided with reference sign 13 in FIG. 4. In general, the holding device 6 can be recesses and/or depressions, more particularly slots or grooves. By way of example, the slits, grooves or depressions can in this case be designed such that the absorber elements 2 can simply be inserted on the edge side with the transverse edges 13, and thus be fixed in their position. Holding device 6 with other designs are feasible, for example projections in the form of pins, strips or the like arranged in pairs. The holding device 6 are situated opposite to one another on the inner sides of the two support elements 4.

Figure 4:
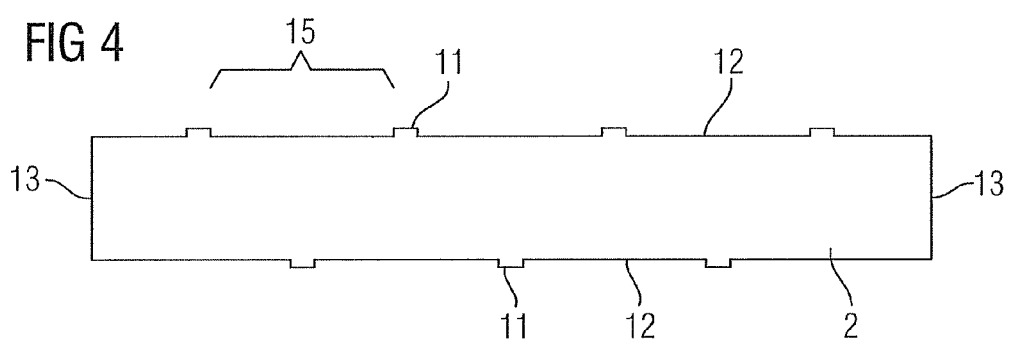
FIG. 4 shows an absorber element with sheet lugs.

Using a positioning tool 14, the absorber elements 2 are aligned precisely with respect to one another and kept in their position for the subsequent production processes for assembling the scattered-radiation collimator 1. For this purpose, the absorber elements 2 have lug-shaped protrusions 11, in this case in the form of sheet lugs, or that are projections arranged distributed over their longitudinal edges 12, as shown in FIG. 4.

Figure 3:
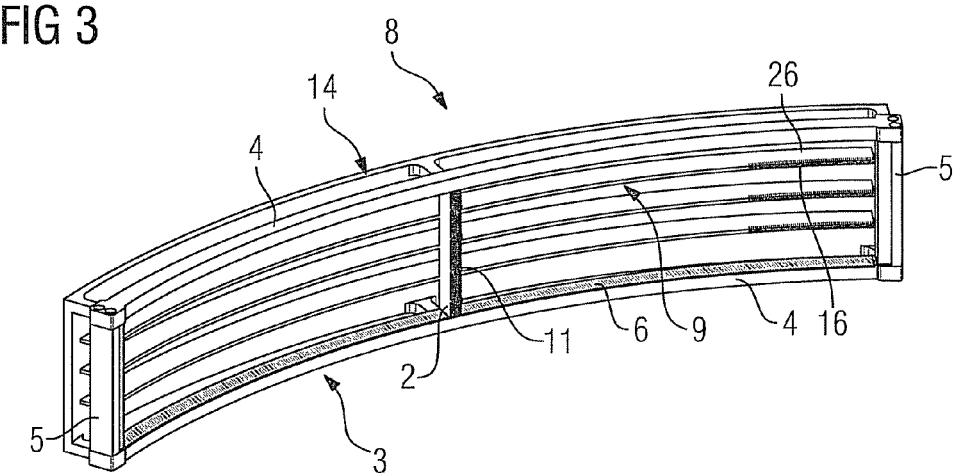
FIG. 3 shows a scattered-radiation collimator according to an embodiment of the invention with inserted absorber elements and with a positioning tool for holding the absorber elements.
Figure 5:
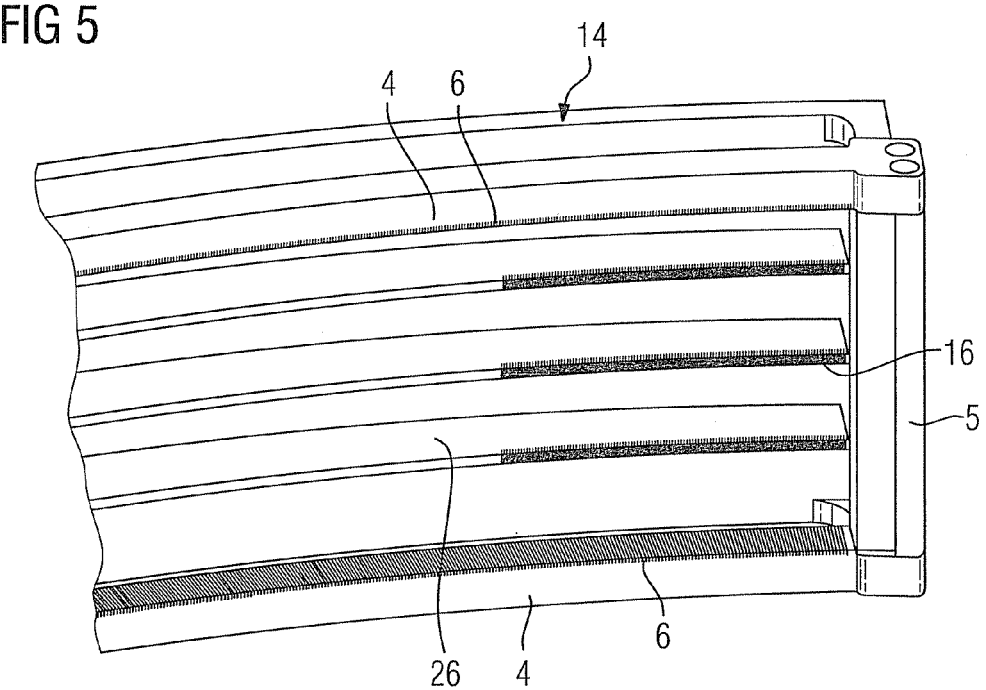
FIG. 5 shows a section of the scattered-radiation collimator shown in FIG. 3.

The positioning tool 14 can be detachably coupled by mechanical means, e.g. by way of corresponding groove, spring or plug connections, to the support frame 3 of the scattered-radiation collimator 1 for producing a defined positional relation with respect to the holding device 6 of the support frame 3, as shown in FIG. 3 and in a detailed section in FIG. 5. The positioning tool 14 has web-shaped positioning elements 26, which extend over the entire scattered-radiation collimator 1 in the collimation direction φ. The positioning elements 26 comprise reception means in the form of slits 16, which correspond to the sheet lugs 11 of the absorber elements 2, on the side facing the scattered-radiation collimator 1. The positioning elements 26 or the sheet lugs of the absorber elements 2 are arranged such that the interspaces 15 between the protrusions 11 are still accessible.

Reference is made to the fact that other holding forms would be feasible instead of the protrusions, e.g. in the form of sheet lugs for the absorber elements 2 and the slits 16 for the positioning elements 26. By way of example, the protrusions 11 at the longitudinal edges 12 of the absorber elements 2 could be dispensed with. This is because the absorber elements 2 could also be inserted into the slits 16 of the positioning elements 26 without the need for a projection if said positioning elements 26 have an appropriate design.

Since high acceleration forces act on the absorber elements 2 in the case of a circular or spiral scan of the object 21 to be examined, during which scan the recording system 18, 22 is rotated about the z-axis at a high rotational speed, there is the risk of the absorber elements 2 being temporarily deformed and displaced if there are no further stabilizing measures. This would lead to erroneous positioning of the absorber elements 2, and this in turn would lead to artifacts in the images.

Figure 6:
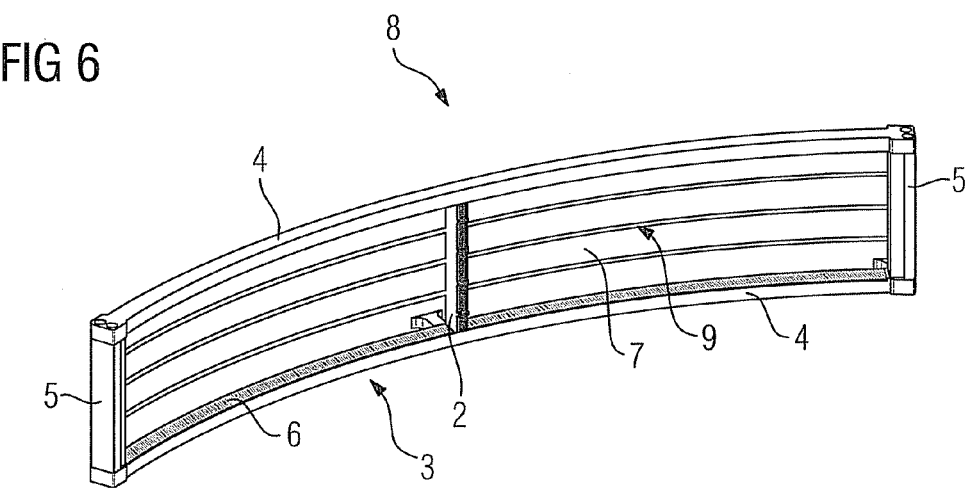
FIG. 6 shows a scattered-radiation collimator with strip-shaped holding elements for fixing the longitudinal edges of the absorber elements, which strip-shaped holding elements are attached to the radiation exit side.

In order to increase the dimensional stability and the positioning accuracy of the absorber elements 2, arc-shaped or bendable holding elements 7 or holding strips are applied to both sides of the scattered-radiation collimator 1, as illustrated initially for the radiation exit side 8 in FIG. 6. The holding strips 7 in this case span all absorber elements 2 in the collimation direction φ and fix their longitudinal edges 12. It would likewise be feasible for the holding strips 7 to be segmented and to extend in each case only over a certain section along the collimation direction φ over part of the absorber elements 2 present. The holding strips 7 penetrated by radiation preferably consist of materials, e.g. CFC or suitable plastics, e.g. LCP, with a low thermal expansion and good X-ray stability with, at the same time, low X-ray absorption so as not to attenuate the useful signal.

The holding strip 7 is coated in advance on one side with an adhesive layer. The adhesive must have low shrinkage properties so that the preset absorber element positions, which were set with the aid of the positioning tool 14, do not change during curing. In particular, epoxy resins highly loaded with mineral compounds lend themselves to this. The adhesive layer is immersed into the compartments made of absorber elements 2, which were prepositioned by the positioning tool 14, and stabilizes the absorber elements 2 after it has cured.

Figure 7:
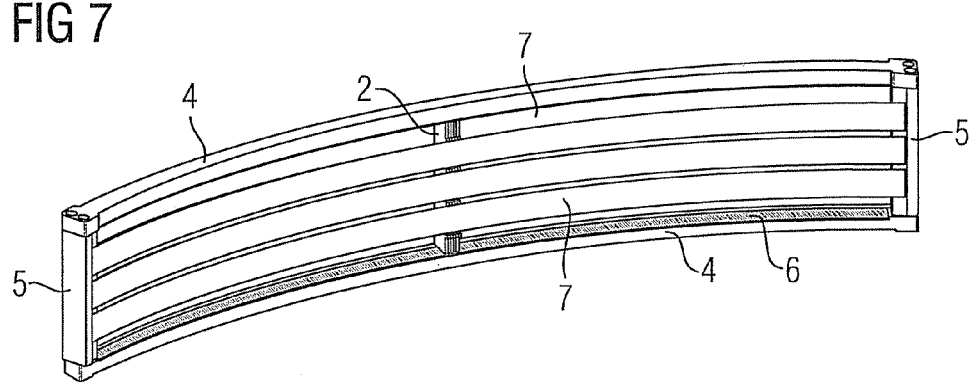
FIG. 7 shows the scattered-radiation collimator shown in FIG. 6 with strip-shaped holding elements for fixing the longitudinal edges of the absorber elements, which strip-shaped holding elements are additionally attached to the radiation entry side.

The holding strips 7 are adhesively attached to both the radiation exit side 8 of the scattered-radiation collimator 1, as shown in FIG. 6, and to its radiation entry side 9, as shown in FIG. 7, and so a torsionally stiff scattered-radiation collimator 1 is produced, in which all four edges 12, 13 of the absorber elements 2 are fixed.

Figure 8:
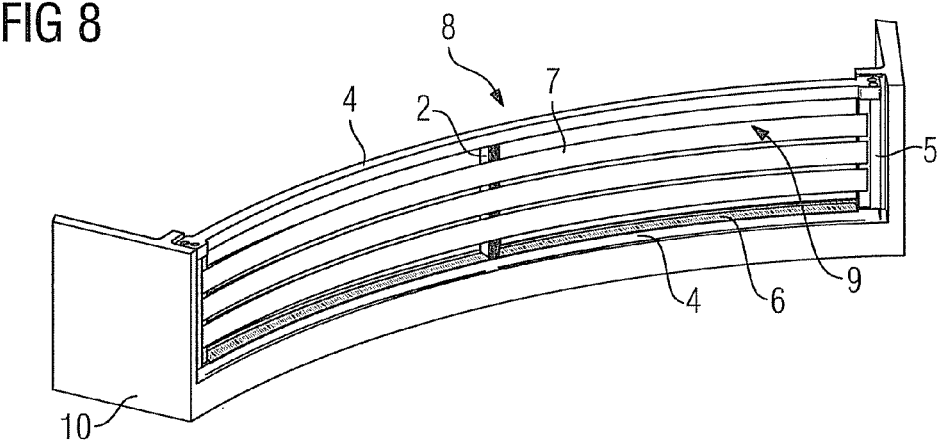
FIG. 8 shows the scattered-radiation collimator shown in FIG. 7 integrated into the radiation detector mechanism.

FIG. 8 shows a completed scattered-radiation collimator 1, which has been installed into the detector mechanism 10.

Although the scattered-radiation collimator described here is described for use in a computed tomography scanner 17 and thus for use with X-ray radiation, the invention is also suitable for use in different modalities, e.g. for PET or SPECT scanners, and for use with different types of radiation, e.g. gamma radiation.

In conclusion, the following statements can be made:

An embodiment of the invention relates to a scattered-radiation collimator 1 for radiological radiation with a multiplicity of absorber elements 2 arranged one behind the other in a collimation direction φ and held in a support frame 3, wherein the support frame 3 has holding device 6 for holding the absorber elements 2 on opposite sides across the collimation direction φ, and wherein at least one strip-like holding element 7 spans the absorber elements 2 in a collimation direction φ on the radiation entry side 9 and/or the radiation exit side 8 of the scattered-radiation collimator 1 and additionally fixes said absorber elements on the longitudinal edges 12 thereof in a mechanical fashion. The holding elements 7 prevent deformations of long absorber elements 2 caused by centrifugal forces to a large extent. This affords the possibility of implementing scattered-radiation collimators 1 with a large Z-coverage that meet the demand on the absorber elements 2 in respect of dimensional stability and positional accuracy. Moreover, the invention relates to a method for producing such a scattered-radiation collimator 1.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A scattered-radiation collimator for radiological radiation comprising:
   a multiplicity of absorber elements, arranged one behind another in a collimation direction;
   at least one strip-like holding element; and
   a support frame to hold the multiplicity of absorber elements, the support frame including a holding device to hold the multiplicity of absorber elements on opposite sides across the collimation direction, wherein the at least one strip-like holding element has an arc shape and spans transversely against longitudinal edges of the multiplicity of absorber elements in the collimation direction on at least one of a radiation entry side and a radiation exit side of the scattered-radiation collimator and additionally fixes the multiplicity of absorber elements on longitudinal edges thereof in a mechanical fashion.

2. The scattered-radiation collimator as claimed in claim 1, wherein the longitudinal edges of the multiplicity of absorber elements include protrusions at least on one of the radiation entry side and radiation exit side of the scattered-radiation collimator, for precisely aligning the multiplicity of absorber elements.

3. The scattered-radiation collimator as claimed in claim 2, wherein, in the collimation direction, the at least one strip-like holding element contacts the plurality of the multiplicity of absorber elements only at an interspace formed by two adjacent protrusions of an absorber element.

4. The scattered-radiation collimator as claimed in claim 2, wherein the protrusions are lug-like projections.

5. The scattered-radiation collimator as claimed in claim 1, wherein the longitudinal edges are fixed to the at least one strip-like holding element by an adhesive.

6. The scattered-radiation collimator as claimed in claim 5, wherein the adhesive has a low shrinkage property.

7. The scattered-radiation collimator as claimed in claim 6, wherein the adhesive has a low shrinkage property as a result of mineral compounds contained in epoxy resins.

8. The scattered-radiation collimator as claimed in claim 1, wherein the at least one strip-like holding element and the support frame are produced from a material with at least one of low thermal expansion and high X-ray stability.

9. The scattered-radiation collimator as claimed in claim 8, wherein the at least one strip-like holding element and the support frame are produced from at least one of a fabric-based laminate, carbon reinforced carbon fiber (CFC) and ceramics.

10. The scattered-radiation collimator as claimed in claim 1, wherein the support frame is formed from two segment-shaped support elements, which extend in the collimation direction and are arranged opposite to one another and at a distance from one another as a result of two spacer elements arranged across the collimation direction.

11. A method for producing a scattered-radiation collimator for radiological radiation including a multiplicity of absorber elements arranged one behind another in a collimation direction, the method comprising:
    positioning the multiplicity of absorber elements in a positioning tool; and
    positioning at least one strip-like holding element, provided with an adhesive and spanning the multiplicity of absorber elements for fixing the multiplicity of absorber elements on the longitudinal edges, on at least one of a radiation entry side and a radiation exit side of the scattered-radiation collimator.

12. The production method as claimed in claim 11, wherein the multiplicity of absorber elements are produced with protrusions, arranged at respectively the same positions along the one longitudinal edge, and wherein the protrusions in the multiplicity of absorber elements matching in terms of the position are inserted into corresponding slits of a positioning element, which extends in the collimation direction of the multiplicity of absorber elements, in the positioning tool.

13. The production method as claimed in claim 12, wherein the holding element is positioned in an interspace, which is between two of the protrusions and formed in each of the multiplicity of absorber elements.

14. The production method as claimed in claim 11, wherein the multiplicity of absorber elements are fixed on the transverse edges by a support frame between the positioning steps or after the second positioning step.

15. The production method as claimed in claim 14, wherein the transverse edges are fixed by inserting the transverse edges into corresponding holding device of the support frame.

16. The production method as claimed in claim 11, wherein the positioning of the multiplicity of absorber elements and the fixing of the multiplicity of absorber elements via a holding element are carried out for opposing longitudinal edges of the multiplicity of absorber elements.

\* \* \* \* \*